United States Patent
Seto et al.

(10) Patent No.: US 7,336,762 B2
(45) Date of Patent: Feb. 26, 2008

(54) SCAN PROGRAM COMMUNICATION METHOD AND X-RAY CT APPARATUS

(75) Inventors: Masaru Seto, Tokyo (JP); Yasushi Sato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 34 days.

(21) Appl. No.: 11/179,872

(22) Filed: Jul. 12, 2005

(65) Prior Publication Data

US 2006/0013358 A1 Jan. 19, 2006

(30) Foreign Application Priority Data

Jul. 15, 2004 (JP) .............................. 2004-208185

(51) Int. Cl.
*G01N 23/00* (2006.01)

(52) U.S. Cl. ......................................... 378/16; 378/110

(58) Field of Classification Search .............. 378/4–20, 378/109, 110, 42, 901
See application file for complete search history.

(56) References Cited

U.S. PATENT DOCUMENTS

| | | | | |
|---|---|---|---|---|
| 5,379,333 A | * | 1/1995 | Toth | 378/16 |
| 5,400,378 A | * | 3/1995 | Toth | 378/16 |
| 5,450,462 A | * | 9/1995 | Toth et al. | 378/16 |
| 5,485,494 A | * | 1/1996 | Williams et al. | 378/16 |
| 6,801,594 B1 | | 10/2004 | Ali et al. | |
| 7,072,437 B2 | * | 7/2006 | Seto | 378/20 |
| 7,145,984 B2 | * | 12/2006 | Nishide | 378/98.5 |
| 2004/0190674 A1 | | 9/2004 | Tsukagoshi | |
| 2004/0247070 A1 | | 12/2004 | Ali et al. | |

FOREIGN PATENT DOCUMENTS

JP 2004-089430 3/2004

* cited by examiner

*Primary Examiner*—Jurie Yun
(74) *Attorney, Agent, or Firm*—Armstrong Teasdale LLP

(57) ABSTRACT

An X-ray CT apparatus includes a host and a scanner that executes a scan based on a scan program communicated from the host by means of communicating means. The X-ray CT apparatus also includes a communicating means which collectively communicate the calculated values of X-ray applied amounts at every scan positions or original data for the calculation of the amount of X-ray application even with respect to unprogrammed scan positions. Each of the calculated values of X-ray applied amounts corresponds to a tube current value of an X-ray tube. The original data for the calculation of the amount of X-ray application corresponds to X-ray penetrated image data of a subject.

16 Claims, 5 Drawing Sheets

SCAN PROGRAM COMMUNICATION METHOD AND X-RAY CT APPARATUS

CROSS REFERENCE TO RELATED APPLICATIONS

This application claims the benefit of Japanese Application No. 2004-208185 filed Jul. 15, 2004.

BACKGROUND OF THE INVENTION

The present invention relates to a scan program communication method and an X-ray CT (computed tomography) apparatus. The present invention relates more specifically to a scan program communication method suitable for use in an X-ray CT apparatus having a host and a scanner and wherein the scanner executes a scan, based on a scan program communicated from the host, and an X-ray CT apparatus wherein a scan program is communicated from a host to a scanner.

In an X-ray CT apparatus, a host creates a scan program and a scanner executes the scan program to collect scan data. A reconstruction engine reconstructs an image from the scan data.

The host comprises a computer, the scanner comprises a gantry and a table, and the reconstruction engine comprises a computer dedicated to image reconstruction. The supply of the scan program from the host to the scanner is performed by communications (refer to, for example, a Patent Document 1).

[Patent Document 1] Japanese Unexamined Patent Publication No. 2004-89430 (4th to 5th pages and FIGS. 1 and 2)

When a scan requiring or calling for a real time property is performed as in the case of, for example, fluoroscopy or the like with respect to each scan position non-contained in the original scan program after execution of a scan based on one scan program, the X-ray CT apparatus reuses the already communicated scan program except for the scan position without transmitting a new scan program.

In such a case, each of the calculated values of X-ray applied amounts employed in the reused scan program is one for the original scan position. Therefore, a scan based on the proper amount of application of X-rays is not necessarily carried out with respect to a new scan position.

SUMMARY OF THE INVENTION

Therefore, an object of the present invention is to realize a scan program communication method which enables a scan based on the proper amount of application of X-rays even when a real time property is required, and an X-ray CT apparatus which executes such a scan program communication.

(1) The invention according to one aspect for solving the above problems provides a scan program communication method suitable for use in an X-ray CT apparatus which has a host and a scanner and causes the scanner to execute a scan, based on a scan program communicated from the host, comprising the step of collectively communicating calculated values of X-ray applied amounts obtained every scan positions or original data for calculation of the amount of X-ray application even with respect to unprogrammed scan positions.

(2) The invention according to another aspect for solving the above problems provides an X-ray CT apparatus comprising a host, and a scanner which executes a scan, based on a scan program communicated from the host by communicating means, wherein the communicating means collectively communicates calculated values of X-ray applied amounts obtained every scan positions or original data for calculation of the amount of X-ray application even with respect to unprogrammed scan positions.

Each of the calculated values of X-ray applied amounts may preferably be a tube current value of an X-ray tube in that the amount of application of X-rays is properly defined.

The original data for the calculation of the amount of X-ray application may preferably be X-ray penetrated image data of a subject in that the calculation of the amount of application of X-rays is performed accurately. Incidentally, the original data for the calculation of the amount of X-ray application is not limited to the X-ray penetrated image data of the subject but may be a data string obtained from computed penetration image data, modeled virtual subject data, or 3D scanning data based on low dose, or the like.

The communication of the calculated values of X-ray applied amounts or the original data for the calculation of the amount of X-ray application may preferably be done together with the communication of the scan program in that the number of communications is reduced.

The communication of the calculated values of X-ray applied amounts or the original data for the calculation of the amount of X-ray application may preferably be carried out prior to the communication of the scan program in terms of adaptation to a prior preparation for the calculated values of X-ray applied amounts or the original data for the calculation of the amount of X-ray application.

The communication of the calculated values of X-ray applied amounts or the original data for the calculation of the amount of X-ray application may preferably be performed behind the communication of the scan program in terms of adaptation to a delay preparation for the calculated values of X-ray applied amounts or the original data for the calculation of the amount of X-ray application.

The scan program may preferably contain programmed values related to scan positions in that the scan positions are defined.

The scan program may preferably contain programmed values related to a tilt scan in that the tilt scan is defined.

In the inventions according to the respective aspects, the calculated values of X-ray applied amounts obtained every scan positions or the original data for the calculation of the amount of X-ray application is collectively communicated even with respect to unprogrammed scan positions. Therefore, a scan program communication method which enables a scan based on the proper amount of X-ray application even in the case where a real time property is required, and an X-ray CT apparatus which performs such a scan program communication, can be realized.

Further objects and advantages of the present invention will be apparent from the following description of the preferred embodiments of the invention as illustrated in the accompanying drawings.

DETAILED DESCRIPTION OF THE INVENTION

Figure 1:
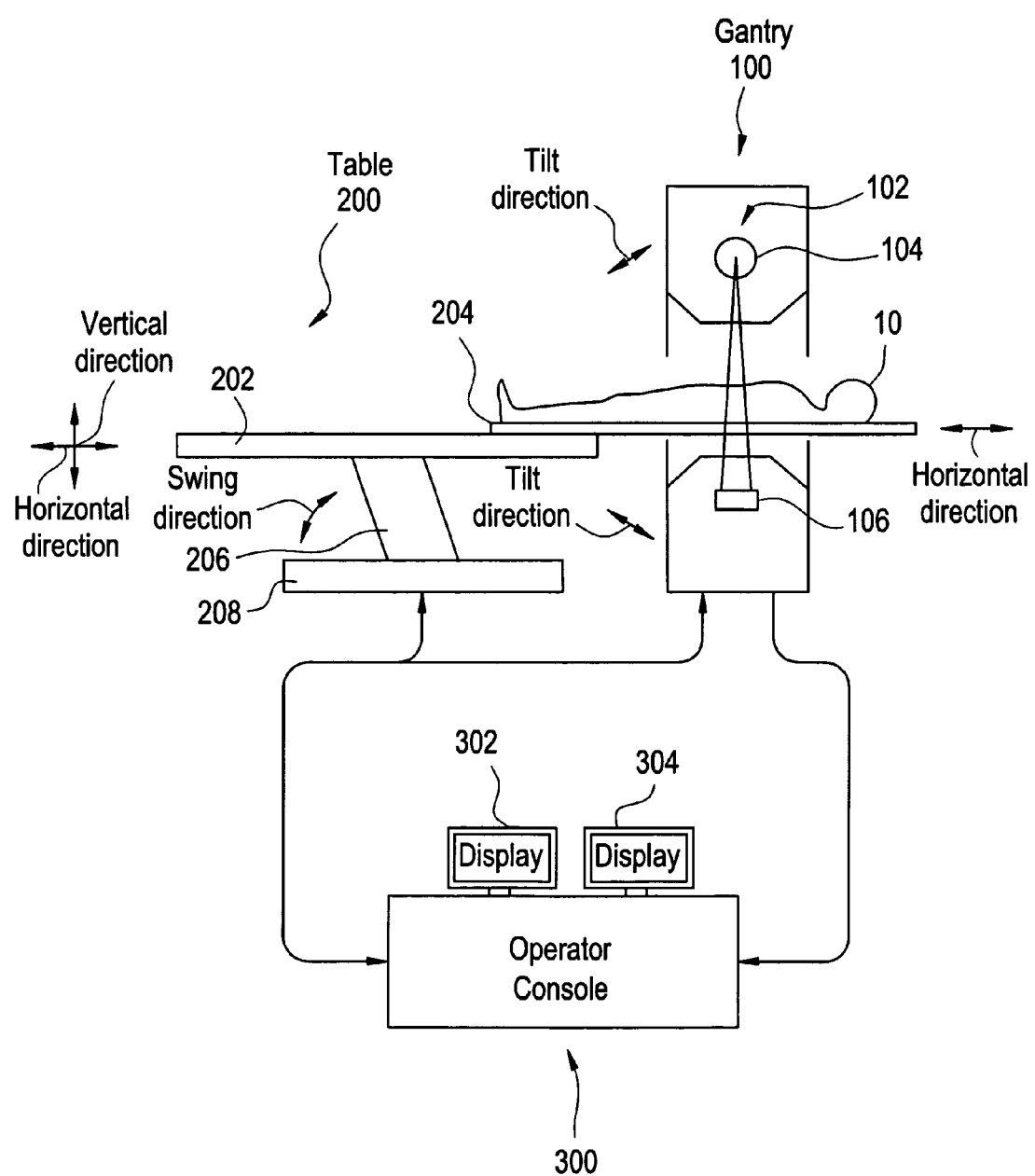
FIG. 1 is a diagram showing a configuration of an X-ray CT apparatus illustrative of one example of the best mode for carrying out the present invention.

Best modes for carrying out the invention will be explained below with reference to the accompanying drawings. Incidentally, the present invention is not limited to the best modes for carrying out the invention. A configuration of an X-ray CT apparatus is shown in FIG. 1. The present apparatus is one example showing the best mode for carrying out the present invention. One example of the best mode for carrying out the present invention related to the X-ray CT apparatus is shown by the configuration of the present apparatus. One example of the best mode for carrying out the present invention related to a scan program communication method is shown by the operation of the present apparatus.

As shown in the same figure, the present apparatus has a gantry 100, a table 200 and an operator console 300. The gantry 100 scans a subject 10 carried in by the table 200 through an X-ray application/detection device 102 to collect scan data. The X-ray application/detection device 102 has an X-ray tube 104 and an X-ray detector 106.

The gantry 100 performs a scan under a predetermined scan condition, and the table 200 positions the subject 10 in a photography space in such a manner that a predetermined region is scanned. The positioning of the subject 10 is performed by adjusting the height of a top table 202 and a horizontal moving distance of a cradle 204 placed thereon by means of a built-in position adjustment mechanism.

An adjustment to the height of the top table 202 is performed by swinging a support or post 206 with a portion attached to a base 208 as the center. With the swing of the post 206, the top table 202 is displaced or shifted in the vertical and horizontal directions. The cradle 204 is displaced horizontally over the top table 202. According to scan conditions, a scan is performed in a state in which the gantry 100 is being tilted. The tilting of the gantry 100 is made by a built-in tilt mechanism.

The operator console 300 gives a scan program to the gantry 100 and the table 200 and causes them to perform a scan based on the scan program. Further, the operator console 300 inputs scan data from the gantry 100 and performs an image reconstruction, based on the scan data. That is, the operator console 300 functions as a host that supplies the scan program to the gantry 100 and the table 200 and functions as an image reconstruction device that reconstructs an image from the scan data.

The operator console 300 has two displays 302 and 304 in association with these two functions. One display 302 thereof is a display for the host, whereas the other display 304 is a display for the image reconstruction device.

Figure 2:
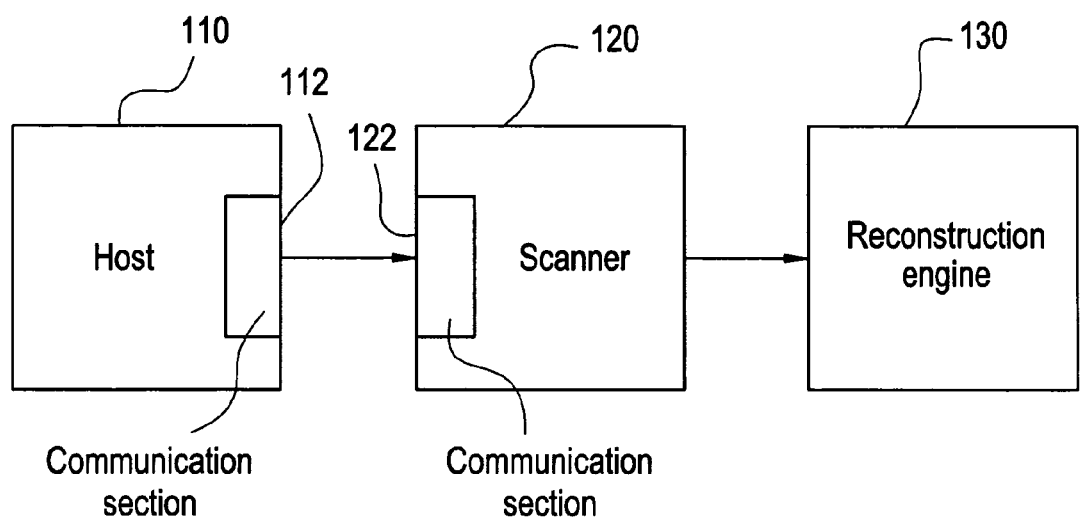
FIG. 2 is a block diagram showing the X-ray CT apparatus illustrative of one example of the best mode for carrying out the present invention as viewed from its functional aspect.

A block diagram of the present apparatus as viewed from the functional aspect is shown in FIG. 2. As shown in the same figure, the present apparatus has a host 110, a scanner 120 and a reconstruction engine 130. The host 110 is one example of a host according to the present invention. The scanner 120 is one example of a scanner according to the present invention.

The host 110 provides or exhibits a host function of the operator console 300. The substance of the host 110 is a host computer built in the operator console 300. The host has a communication section 112 and transmits a scan program to the scanner 120 through the communication section. The communication section 112 is one example of communicating means according to the present invention.

The scanner 120 provides or exhibits the functions of the gantry 100 and the table 200. The scanner 120 has a communication section 122 corresponding to the communication section 112 of the host 110 and receives the corresponding scan program through the communication section 122. The communication section 122 is one example of communicating means according to the present invention. The scanner 120 executes a scan in accordance with the received scan program and inputs collected scan data to the reconstruction engine 130.

The reconstruction engine 130 provides or exhibits an image reconstruction function of the operator console 300. The substance of the reconstruction engine 130 is a computer dedicated to the image reconstruction, which has been built in the operator console 300.

Figure 3:
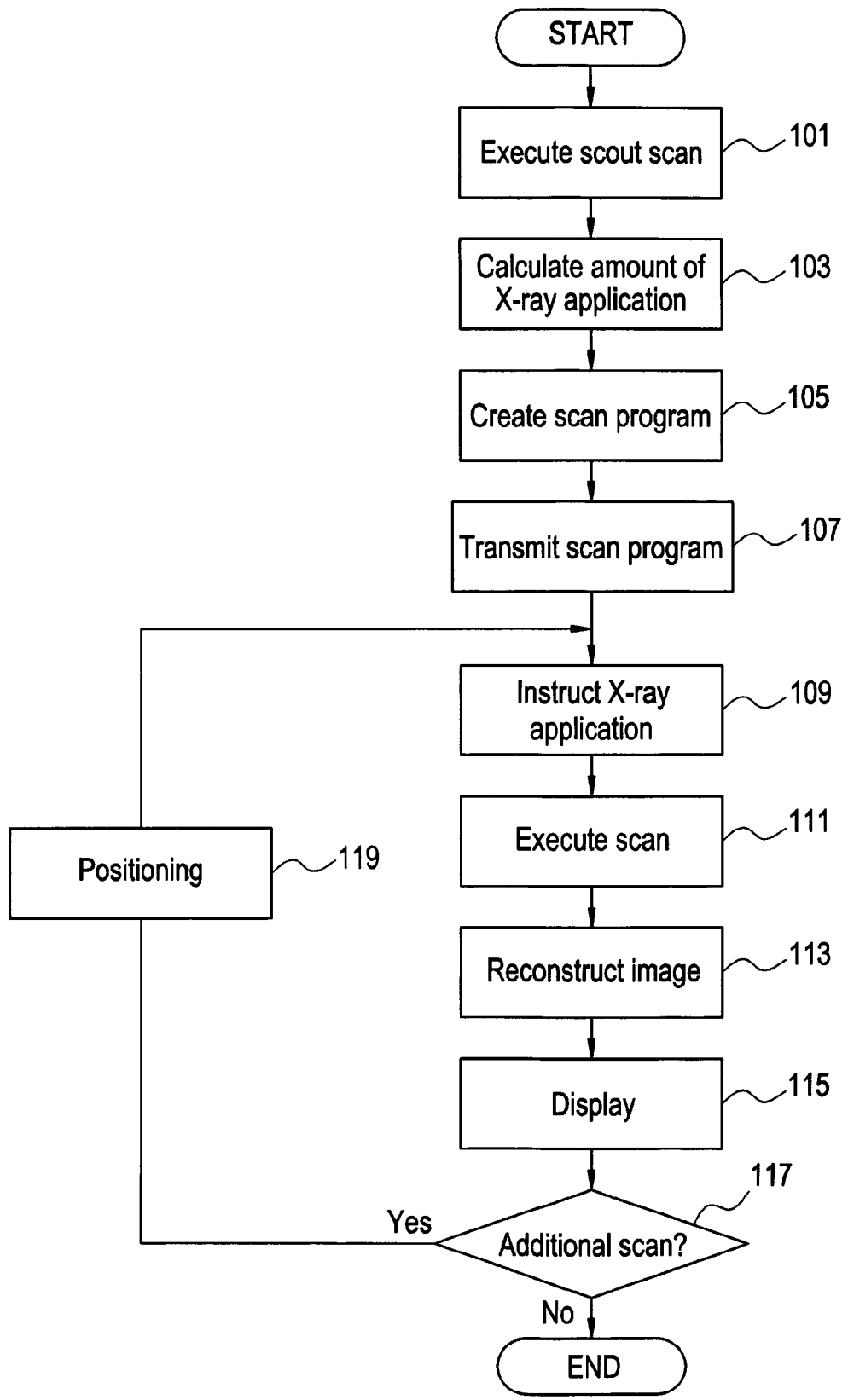
FIG. 3 is a flow diagram for describing the operation of the X-ray CT apparatus illustrative of one example of the best mode for carrying out the present invention.

A flow diagram illustrating the operation of the present apparatus is shown in FIG. 3. As shown in the same figure, a scout scan is performed in Step 101. The scout scan is carried out by photographing a penetration image while continuously carrying the subject 10 in its body-axis direction in a state in which the direction of irradiation or application of X-rays has been fixed to the front or side direction of the subject 10, for example.

Next, the amount of application of X-rays is calculated in Step 103. Data about the penetration image of the subject 10, which has been obtained by the scout scan, is used for the calculation of the amount of application of X-rays. The amount of X-ray application is determined as a tube current of the X-ray tube. The optimum value is determined for each position on the body axis of the subject 10 as the tube current. Incidentally, the optimum value indicates the minimum amount of application of X-rays in the allowable range of photography quality.

The tube currents determined every positions result in ones modulated according to the rotational angles of the X-ray tube while being in scan. When a tilt scan is carried out, a tube current corresponding to it is calculated. Such a tube current calculating method using the penetration image data is already known in the corresponding technical field and is commonly called "auto-mA".

Next, a scan program is created in Step 105. The creation of the scan program is performed using the operator console 300 by an operator of the present apparatus. The operator determines a position to scan the subject 10 and creates a scan program for scanning the position. The scan program includes set values related to, for example, scan positions, a tilt angle, tube voltages, tube currents, scan FOV (field of view), etc. Each calculated value referred to above is used as a tube-current programmed value.

Next, scan program transmission is carried out in Step 107. The transmission of the scan program is carried out between the host 110 and the scanner 120 through the communication sections 112 and 122. At this time, tube-current calculated values are transmitted together even with respect to unprogrammed scan positions.

Figure 4:
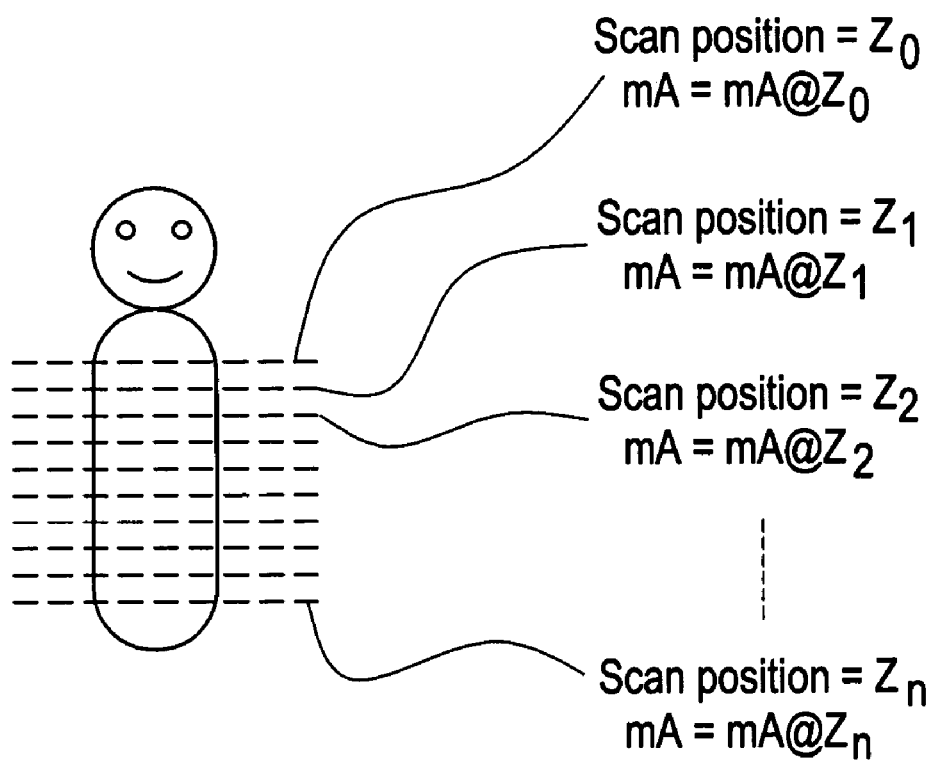
FIG. 4 is a diagram showing combinations of scan positions and tube currents.

That is, assuming that as shown in FIG. 4 by way of example, the scan position is Z0 and the tube current corresponding to it is mA@Z0 in terms of a scan program, a scan program with these as the contents is transmitted. Even with respect to a plurality of scan positions Z1, Z2, . . . , Zn unset to the scan program, tube-current calculated values mA@Z1, mA@Z2, . . . , mA@Zn set every scan positions are transmitted with the scan program.

Incidentally, the programmed scan position is not limited to Z0 but may be any of the scan positions from Z1 to Zn. The programmed scan position is not limited to one location but may be set to plural locations. In any case, the scan positions other than it result in the scan positions out of the program.

Next, the application of X rays is instructed in Step 109. The operator presses an application button on the operator console 300 or an application button attached to the gantry 100 to give the X-ray application instruction.

Figure 5:
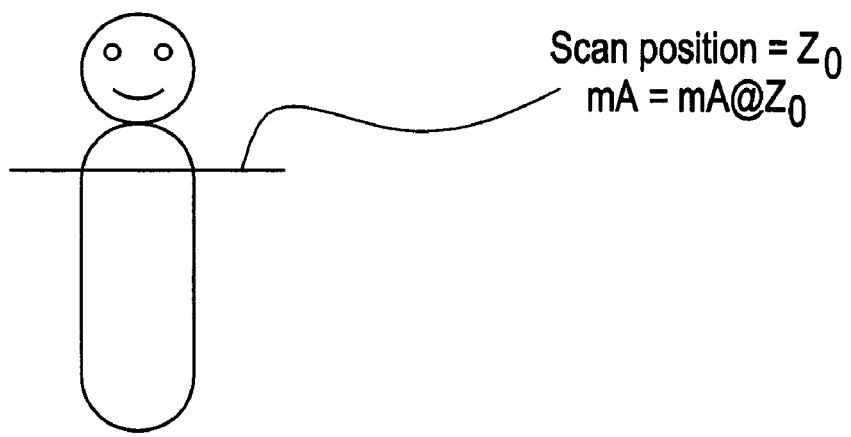
FIG. 5 is a diagram illustrating a scan based on a scan program.

Thus, a scan is executed in Step 111. The scan is carried out in accordance with the scan program by the scanner 120. Consequently, the scan is effected on a scan position Z0 with a tube current mA@Z0 as shown in FIG. 5, for example.

Then, an image reconstruction is performed in Step S113. The reconstructed image is displayed in Step 115. The image reconstruction is done by the reconstruction engine 130, and the display of the reconstructed image is made by the display 304.

The operator confirms the result of execution of the scan program through the reconstructed image displayed on the display 304. An additional scan might be required according to whether the result is good or bad. In such a case, positioning for the additional scan is done in Step 119 on the basis of a judgement made in Step 117.

Figure 6:
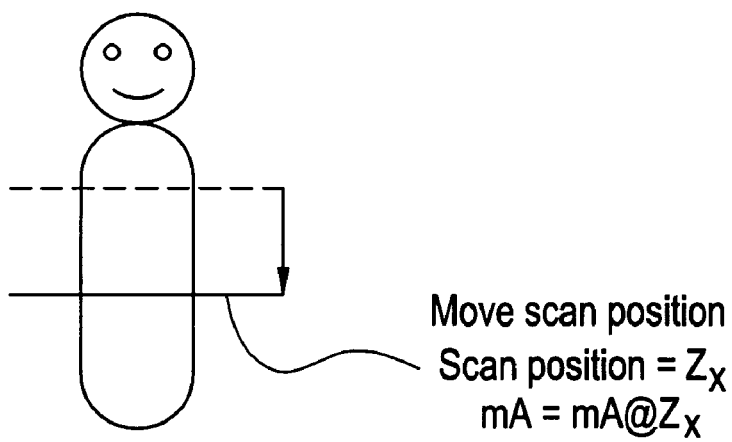
FIG. 6 is a diagram depicting a scan out of a scan program.

Thus, a scan position Zx unset to the original scan program is set as shown in FIG. 6, for example. In regard to the scan position Zx, the tube-current calculated value mA@Zx corresponding to it has already been transmitted from the host 110 to the scanner 120 in Step 107.

Thus, when the application of X rays is instructed in Step 109, a scan based on the tube-current calculated value mA@Zx is performed in Step 111. That is, the scan based on the amount of X-ray application optimal to the scan position Zx is executed.

Since the tube-current calculated value mA@Zx has already been transmitted from the host 110 to the scanner 120 in this way before the start of the additional scan, the additional scan can be executed immediately. Further, the scan can be carried out in accordance with the amount of X-ray application optimal to the scan position Zx. Thus, even when a real time property is required, a scan based on the proper amount of X-ray application can be performed.

Therefore, fluoroscopy can be effectively carried out by the present apparatus. When the subject 10 is biopsied, the present apparatus is suitable even for an application which obtains a real-time tomogram of a desired region. Further, even when a portion prior or subsequent to a photography range is found to be short of scan after the completion of the scan program, the deficient scan, i.e., a so-called one more scan can be performed immediately.

Even when the scan is started in the optimum timing while monitoring the condition of dyeing of a contrast agent in a region of interest upon contrast photography, the real time property of the present invention is effective. Even it is necessary to scan the last group once again (repeat last group) after the temporary completion of the contrast photography, the real time property of the present invention is of great utility.

Since each of the calculated values of X-ray applied amounts corresponds to the tube current value of the X-ray tube in the present apparatus, the amount of X-ray application can be prescribed properly. Incidentally, one transmitted from the host to the scanner may be set as original data for the calculation of the amount of X-ray application, and the scanner may be caused to calculate the tube current. This execution makes it easy to adapt to a case in which the additional scan is carried out in the form of a tilt scan. In such a case, the original data for the calculation of the amount of X-ray application is set as X-ray penetrated image data of the subject, thereby making it possible to accurately calculate the amount of X-ray application.

Incidentally, the original data for the calculation of the amount of X-ray application is not limited to the X-ray penetrated image data of the subject. The original data may be data enough to calculate tube currents, such as a data string obtained from computed penetration image data, modeled virtual subject data, or 3D scanning data based on low dose, or the like. Alternatively, the original data may be a file name indicative of penetration image data. Further, if the scanner calculates a tube current with respect to the latest scout image, then the host needs not send penetration image data or the like to the scanner and may simply send parameters necessary for tube current calculation.

Since the calculated values of X-ray applied amounts or the original data for the calculation of the amount of X-ray application is communicated together with the communication of the scan program, the number of communications can be reduced in the present apparatus. Incidentally, the communication of the calculated values of X-ray applied amounts or the communication of the original data for the calculation of the amount of X-ray application may be done prior to the communication of the scan program. Thus, the present apparatus is capable of adapting to a prior preparation for each of the calculated values of X-ray applied amounts or the original data for the calculation of the amount of X-ray application. Alternatively, each of the calculated values of X-ray applied amounts or the original data for the calculation of the amount of X-ray application may be communicated behind the communication of the scan program. Consequently, the present apparatus is capable of adapting to a delay preparation for the calculated value of X-ray applied amount or the original data for the calculation of the amount of X-ray application.

Further, since the scan program contains a programmed value related to each scan position in the present apparatus, the corresponding scan position can be prescribed or defined. Since the scan program includes a programmed value related to a tilt scan, the tilt scan can be prescribed.

Many widely different embodiments of the invention may be configured without departing from the spirit and the scope of the present invention. It should be understood that the present invention is not limited to the specific embodiments described in the specification, except as defined in the appended claims.

The invention claimed is:

1. A scan schedule communication method suitable for scanning an object using an X-ray CT apparatus comprising a host computer and a scanner, wherein the apparatus activates the scanner to execute a scan that is based on a scan schedule communicated from the host computer, said method comprising the steps of:

inputting a scheduled scan range into the host computer;
communicating from the host computer to the scanner at least one of calculated values of X-ray applied amounts for respective scan positions and original data for calculation of X-ray applied amounts for respective scan positions inside the scheduled scan range and at least one of calculated values of X-ray applied amounts for respective scan positions and original data for calculation of X-ray applied amounts for respective scan positions outside the scheduled scan range to facilitate scanning an object with a calculated amount of X-ray application.

2. The scan schedule communication method according to claim 1, wherein each of the calculated values of X-ray applied amounts is a tube current value of an X-ray tube.

3. The scan schedule communication method according to claim 1, wherein the original data for the calculation of the X-ray applied amounts is X-ray penetrated image data of a subject.

4. The scan schedule communication method according to claim 1, wherein the communication of the calculated values of X-ray applied amounts or the original data for the calculation of the X-ray applied amounts are done together with the communication of the scan schedule.

5. The scan schedule communication method according to claim 4, wherein the scan schedule contains programmed values related to scan positions.

6. The scan schedule communication method according to claim 4, wherein the scan schedule contains programmed values related to a tilt scan.

7. The scan schedule communication method according to claim 1, wherein the communication of the calculated values of X-ray applied amounts or the original data for the calculation of the X-ray applied amounts are carried out prior to the communication of the scan schedule.

8. The scan schedule communication method according to claim 1, wherein the communication of the calculated values of X-ray applied amounts or the original data for the calculation of the X-ray applied amounts are performed behind the communication of the scan schedule.

9. An X-ray CT apparatus comprising:
a host computer including scan schedule information and at least one of calculated values of X-ray applied amounts for respective scan positions and original data for calculation of X-ray applied amounts for respective scan positions;
a scanner for executing a scan that is based on the scan schedule information; and
a communicating device for communicating the schedule information from the host computer to the scanner,
wherein the communicating device includes a first communicating section for communicating at least one of calculated values of X-ray applied amounts for respective scan positions and original data for calculation of X-ray applied amounts for respective scan positions inside a scheduled scan range and a second communicating section for communicating at least one of calculated values of X-ray applied amounts for respective scan positions and original data for calculation of X-ray applied amounts for respective scan positions outside the scheduled scan range.

10. The X-ray CT apparatus according to claim 9, wherein each of the calculated values of X-ray applied amounts is a tube current value of an X-ray tube.

11. The X-ray CT apparatus according to claim 9, wherein the original data for the calculation of the X-ray applied amounts is X-ray penetrated image data of a subject.

12. The X-ray CT apparatus according to claim 9, wherein the communication of the calculated values of X-ray applied amounts or the original data for the calculation of the X-ray applied amounts are done together with the communication of the scan schedule.

13. The X-ray CT apparatus according to claim 12, wherein the scan schedule contains programmed values related to scan positions.

14. The X-ray CT apparatus according to claim 12, wherein the scan schedule contains programmed values related to a tilt scan.

15. The X-ray CT apparatus according to claim 9, wherein the communication of the calculated values of X-ray applied amounts or the original data for the calculation of the X-ray applied amounts are carried out prior to the communication of the scan schedule.

16. The X-ray CT apparatus according to claim 9, wherein the communication of the calculated values of X-ray applied amounts or the original data for the calculation of X-ray applied amounts are performed behind the communication of the scan schedule.

* * * * *